(12) United States Patent
Taylor

(10) Patent No.: US 7,776,069 B2
(45) Date of Patent: Aug. 17, 2010

(54) POSTERIOR VERTEBRAL SUPPORT ASSEMBLY

(75) Inventor: Jean Taylor, Eden Palace (FR)

(73) Assignee: Kyphon SÀRL, Neuchâtel (CH)

( * ) Notice: Subject to any disclaimer, the term of this patent is extended or adjusted under 35 U.S.C. 154(b) by 209 days.

(21) Appl. No.: 10/527,251

(22) PCT Filed: Sep. 3, 2003

(86) PCT No.: PCT/FR03/02635

§ 371 (c)(1),
(2), (4) Date: Mar. 9, 2005

(87) PCT Pub. No.: WO2004/024010

PCT Pub. Date: Mar. 25, 2004

(65) Prior Publication Data

US 2006/0136060 A1     Jun. 22, 2006

(30) Foreign Application Priority Data

Sep. 10, 2002  (FR) .................................. 02 11189

(51) Int. Cl.
*A61B 17/70*  (2006.01)
(52) U.S. Cl. .................................................... 606/249
(58) Field of Classification Search ................... 606/60, 606/61; 623/17.11–17.13, 17.16, 6.43
See application file for complete search history.

(56) References Cited

U.S. PATENT DOCUMENTS

| 2,077,804 | A | 4/1937 | Morrison |
| 2,677,369 | A | 5/1954 | Knowles |
| 3,426,364 | A | 2/1969 | Lumb |
| 3,648,691 | A | 3/1972 | Lumb et al. |
| 3,779,239 | A | 12/1973 | Fischer et al. |
| 4,011,602 | A | 3/1977 | Rybicki et al. |

(Continued)

FOREIGN PATENT DOCUMENTS

DE     2821678 A1     11/1979

(Continued)

OTHER PUBLICATIONS

"Dispositivo Intervertebrale Ammortizzante DIAM," date unknown, p. 1.

(Continued)

*Primary Examiner*—Thomas C Barrett
*Assistant Examiner*—Nicholas Woodall
(74) *Attorney, Agent, or Firm*—Coats and Bennett, P.L.L.C.

(57) ABSTRACT

The invention concerns an assembly (1) comprising an interspinous wedge (5) configured to be inserted between the spinous processes (9) of two vertebrae (2) to be treated, whereof at least one zone designed to be placed between the spinous processes of the vertebrae is made of an elastically deformable material. The assembly (1) further comprises: two compressive lateral elements (6), designed to be placed on either side of the wedge (5) in the longitudinal direction, said compressive lateral elements (6) being deformable between releasing positions, wherein they are relatively spaced apart from the wedge (5) in the transverse direction, and compressive positions, wherein they are relatively close to the wedge (5) in the transverse direction; and two lateral transmission elements (7), placed between the compressive lateral elements (6) and the wedge (5), configured to press against the wedge (5) in the transverse direction thereof, at the interspinous zone (10) of the wedge (5).

15 Claims, 1 Drawing Sheet

U.S. PATENT DOCUMENTS

| Patent Number | | Date | Inventor(s) |
|---|---|---|---|
| 4,237,875 | A | 12/1980 | Termanini |
| 4,257,409 | A | 3/1981 | Bacal et al. |
| 4,289,123 | A | 9/1981 | Dunn |
| 4,401,112 | A | 8/1983 | Rezaian |
| 4,553,273 | A | 11/1985 | Wu |
| 4,554,914 | A | 11/1985 | Kapp et al. |
| 4,573,454 | A | 3/1986 | Hoffman |
| 4,599,086 | A | 7/1986 | Doty |
| 4,604,995 | A | 8/1986 | Stephens et al. |
| 4,611,582 | A | 9/1986 | Duff |
| 4,632,101 | A | 12/1986 | Freedland |
| 4,636,217 | A | 1/1987 | Ogilvie et al. |
| 4,657,550 | A | 4/1987 | Daher |
| 4,686,970 | A | 8/1987 | Dove et al. |
| 4,759,769 | A | 7/1988 | Hedman et al. |
| 4,827,918 | A | 5/1989 | Olerud |
| 4,863,476 | A | 9/1989 | Shepperd |
| 4,886,405 | A | 12/1989 | Blomberg |
| 4,892,545 | A | 1/1990 | Day et al. |
| 4,913,144 | A | 4/1990 | Del Medico |
| 4,931,055 | A | 6/1990 | Bumpus et al. |
| 4,932,975 | A | 6/1990 | Main et al. |
| 4,969,887 | A | 11/1990 | Sodhi |
| 5,011,484 | A | 4/1991 | Breard |
| 5,047,055 | A | 9/1991 | Bao et al. |
| 5,059,193 | A | 10/1991 | Kuslich |
| 5,092,866 | A | 3/1992 | Breard et al. |
| 5,098,433 | A | 3/1992 | Freedland |
| 5,171,278 | A | 12/1992 | Pisharodi |
| 5,201,734 | A | 4/1993 | Cozad et al. |
| 5,290,312 | A | 3/1994 | Kojimoto et al. |
| 5,306,275 | A | 4/1994 | Bryan |
| 5,306,297 | A * | 4/1994 | Rheinish et al. ............ 623/6.43 |
| 5,306,310 | A | 4/1994 | Siebels |
| 5,312,405 | A | 5/1994 | Korotko et al. |
| 5,360,430 | A | 11/1994 | Lin |
| 5,366,455 | A | 11/1994 | Dove |
| 5,390,683 | A | 2/1995 | Pisharodi |
| 5,395,370 | A | 3/1995 | Muller et al. |
| 5,403,316 | A | 4/1995 | Ashman |
| 5,415,661 | A | 5/1995 | Holmes |
| 5,437,672 | A | 8/1995 | Alleyne |
| 5,437,674 | A | 8/1995 | Worcel et al. |
| 5,454,812 | A | 10/1995 | Lin |
| 5,458,641 | A | 10/1995 | Ramirez |
| 5,496,318 | A * | 3/1996 | Howland et al. ............... 606/61 |
| 5,518,498 | A | 5/1996 | Lindenberg et al. |
| 5,540,688 | A | 7/1996 | Navas |
| 5,554,191 | A | 9/1996 | Lahille et al. |
| 5,562,662 | A | 10/1996 | Brumfield et al. |
| 5,562,735 | A | 10/1996 | Margulies |
| 5,609,634 | A | 3/1997 | Voydeville |
| 5,609,635 | A | 3/1997 | Michelson |
| 5,628,756 | A | 5/1997 | Barker, Jr. et al. |
| 5,630,816 | A | 5/1997 | Kambin |
| 5,645,599 | A * | 7/1997 | Samani ..................... 623/17.16 |
| 5,653,762 | A | 8/1997 | Pisharodi |
| 5,653,763 | A | 8/1997 | Errico et al. |
| 5,658,335 | A | 8/1997 | Allen |
| 5,665,122 | A | 9/1997 | Kambin |
| 5,674,295 | A | 10/1997 | Ray et al. |
| 5,676,702 | A | 10/1997 | Ratron |
| 5,690,649 | A | 11/1997 | Li |
| 5,693,100 | A | 12/1997 | Pisharodi |
| 5,702,395 | A | 12/1997 | Hopf |
| 5,702,452 | A | 12/1997 | Argenson et al. |
| 5,702,455 | A | 12/1997 | Saggar |
| 5,707,390 | A | 1/1998 | Bonutti |
| 5,716,416 | A | 2/1998 | Lin |
| 5,723,013 | A | 3/1998 | Jeanson et al. |
| 5,746,762 | A | 5/1998 | Bass |
| 5,755,797 | A | 5/1998 | Baumgartner |
| 5,800,547 | A | 9/1998 | Schafer et al. |
| 5,810,815 | A | 9/1998 | Morales |
| 5,836,948 | A | 11/1998 | Zucherman et al. |
| 5,849,004 | A | 12/1998 | Bramlet |
| 5,860,977 | A | 1/1999 | Zucherman et al. |
| 5,888,196 | A | 3/1999 | Bonutti |
| 5,976,186 | A | 11/1999 | Bao et al. |
| 6,022,376 | A | 2/2000 | Assell et al. |
| 6,048,342 | A | 4/2000 | Zucherman et al. |
| 6,068,630 | A | 5/2000 | Zucherman et al. |
| 6,126,689 | A | 10/2000 | Brett |
| 6,126,691 | A | 10/2000 | Kasra et al. |
| 6,127,597 | A | 10/2000 | Beyar et al. |
| 6,132,464 | A | 10/2000 | Martin |
| 6,152,959 | A * | 11/2000 | Portney ..................... 623/6.51 |
| 6,190,413 | B1 | 2/2001 | Sutcliffe |
| 6,190,414 | B1 | 2/2001 | Young |
| 6,214,050 | B1 | 4/2001 | Huene |
| 6,293,949 | B1 | 9/2001 | Justis et al. |
| 6,336,930 | B1 | 1/2002 | Stalcup et al. |
| 6,348,053 | B1 | 2/2002 | Cachia |
| 6,352,537 | B1 | 3/2002 | Strnad |
| 6,364,883 | B1 | 4/2002 | Santilli |
| 6,371,987 | B1 | 4/2002 | Weiland et al. |
| 6,375,682 | B1 | 4/2002 | Fleischmann et al. |
| 6,402,750 | B1 | 6/2002 | Atkinson et al. |
| 6,402,751 | B1 | 6/2002 | Hoeck et al. |
| 6,419,704 | B1 | 7/2002 | Ferree |
| 6,440,169 | B1 * | 8/2002 | Elberg et al. ............. 623/17.16 |
| 6,447,513 | B1 | 9/2002 | Griggs |
| 6,451,019 | B1 | 9/2002 | Zucherman et al. |
| 6,500,178 | B2 * | 12/2002 | Zucherman et al. ........... 606/61 |
| 6,514,256 | B2 * | 2/2003 | Zucherman et al. ........... 606/61 |
| 6,520,991 | B2 | 2/2003 | Huene |
| 6,554,833 | B2 | 4/2003 | Levy et al. |
| 6,582,433 | B2 | 6/2003 | Yun |
| 6,582,467 | B1 | 6/2003 | Teitelbaum et al. |
| 6,592,585 | B2 | 7/2003 | Lee et al. |
| 6,626,944 | B1 * | 9/2003 | Taylor ..................... 623/17.16 |
| 6,645,207 | B2 | 11/2003 | Dixon et al. |
| 6,685,742 | B1 | 2/2004 | Jackson |
| 6,695,842 | B2 | 2/2004 | Zucherman et al. |
| 6,709,435 | B2 | 3/2004 | Lin |
| 6,723,126 | B1 | 4/2004 | Berry |
| 6,730,126 | B2 | 5/2004 | Boehm, Jr. et al. |
| 6,733,534 | B2 | 5/2004 | Sherman |
| 6,736,818 | B2 | 5/2004 | Perren et al. |
| 6,758,863 | B2 | 7/2004 | Estes et al. |
| 6,761,720 | B1 | 7/2004 | Senegas |
| 6,770,096 | B2 | 8/2004 | Bolger et al. |
| 6,783,530 | B1 | 8/2004 | Levy |
| 6,835,205 | B2 | 12/2004 | Atkinson et al. |
| 6,905,512 | B2 | 6/2005 | Paes et al. |
| 6,946,000 | B2 | 9/2005 | Senegas et al. |
| 6,981,975 | B2 | 1/2006 | Michelson |
| 7,011,685 | B2 | 3/2006 | Arnin et al. |
| 7,041,136 | B2 | 5/2006 | Goble et al. |
| 7,048,736 | B2 | 5/2006 | Robinson et al. |
| 7,081,120 | B2 | 7/2006 | Li et al. |
| 7,087,083 | B2 | 8/2006 | Pasquet et al. |
| 7,097,648 | B1 | 8/2006 | Globerman et al. |
| 7,101,375 | B2 | 9/2006 | Zucherman et al. |
| 7,163,558 | B2 | 1/2007 | Senegas et al. |
| 7,201,751 | B2 | 4/2007 | Zucherman et al. |
| 7,217,293 | B2 | 5/2007 | Branch, Jr. |
| 7,238,204 | B2 | 7/2007 | Le Couedic et al. |
| 7,306,628 | B2 | 12/2007 | Zucherman et al. |
| 7,377,942 | B2 | 5/2008 | Berry |
| 7,442,208 | B2 | 10/2008 | Mathieu et al. |
| 7,445,637 | B2 | 11/2008 | Taylor |
| 7,458,981 | B2 | 12/2008 | Fielding et al. |
| 7,582,106 | B2 | 9/2009 | Teitelbaum et al. |

| | | | |
|---|---|---|---|
| 7,611,316 B2 | 11/2009 | Panasik et al. | |
| 2001/0016743 A1* | 8/2001 | Zucherman et al. | 606/61 |
| 2002/0143331 A1 | 10/2002 | Zucherman et al. | |
| 2003/0045940 A1* | 3/2003 | Eberlein et al. | 623/17.16 |
| 2003/0109880 A1* | 6/2003 | Shirado et al. | 606/61 |
| 2003/0153915 A1 | 8/2003 | Nekozuka et al. | |
| 2003/0220643 A1* | 11/2003 | Ferree | 606/61 |
| 2004/0024458 A1* | 2/2004 | Senegas et al. | 623/17.11 |
| 2004/0097931 A1 | 5/2004 | Mitchell | |
| 2004/0106995 A1 | 6/2004 | Le Couedic et al. | |
| 2004/0117017 A1* | 6/2004 | Pasquet et al. | 623/17.11 |
| 2004/0133204 A1 | 7/2004 | Davies | |
| 2004/0167625 A1 | 8/2004 | Beyar et al. | |
| 2004/0199255 A1* | 10/2004 | Mathieu et al. | 623/17.11 |
| 2004/0260397 A1 | 12/2004 | Lambrecht et al. | |
| 2005/0010293 A1 | 1/2005 | Zucherman et al. | |
| 2005/0033434 A1 | 2/2005 | Berry | |
| 2005/0049708 A1 | 3/2005 | Atkinson et al. | |
| 2005/0165398 A1 | 7/2005 | Reiley | |
| 2005/0203512 A1 | 9/2005 | Hawkins et al. | |
| 2005/0203624 A1 | 9/2005 | Serhan et al. | |
| 2005/0228391 A1 | 10/2005 | Levy et al. | |
| 2005/0245929 A1* | 11/2005 | Winslow et al. | 606/61 |
| 2005/0245937 A1 | 11/2005 | Winslow | |
| 2005/0261768 A1* | 11/2005 | Trieu | 623/17.11 |
| 2005/0288672 A1 | 12/2005 | Feree | |
| 2006/0004447 A1 | 1/2006 | Mastrorio et al. | |
| 2006/0004455 A1 | 1/2006 | Leonard et al. | |
| 2006/0015181 A1 | 1/2006 | Elberg | |
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0085070 A1 | 4/2006 | Kim | |
| 2006/0085074 A1 | 4/2006 | Raiszadeh | |
| 2006/0089654 A1 | 4/2006 | Lins et al. | |
| 2006/0089719 A1 | 4/2006 | Trieu | |
| 2006/0095136 A1 | 5/2006 | McLuen | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0116690 A1 | 6/2006 | Pagano | |
| 2006/0122620 A1 | 6/2006 | Kim | |
| 2006/0129239 A1* | 6/2006 | Kwak | 623/17.13 |
| 2006/0136060 A1 | 6/2006 | Taylor | |
| 2006/0184247 A1* | 8/2006 | Edidin et al. | 623/17.11 |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0235387 A1 | 10/2006 | Peterman | |
| 2006/0235532 A1 | 10/2006 | Meunier et al. | |
| 2006/0241601 A1 | 10/2006 | Trautwein et al. | |
| 2006/0241613 A1 | 10/2006 | Bruneau et al. | |
| 2006/0247623 A1 | 11/2006 | Anderson et al. | |
| 2006/0247640 A1 | 11/2006 | Blackwell et al. | |
| 2006/0264938 A1 | 11/2006 | Zucherman et al. | |
| 2006/0271044 A1 | 11/2006 | Petrini et al. | |
| 2006/0271049 A1 | 11/2006 | Zucherman et al. | |
| 2006/0293662 A1 | 12/2006 | Boyer, II et al. | |
| 2006/0293663 A1 | 12/2006 | Walkenhorst et al. | |
| 2007/0043362 A1 | 2/2007 | Malandain et al. | |
| 2007/0142915 A1 | 6/2007 | Altarac et al. | |
| 2007/0151116 A1 | 7/2007 | Malandain | |
| 2007/0162000 A1 | 7/2007 | Perkins | |
| 2007/0191838 A1 | 8/2007 | Bruneau et al. | |
| 2007/0198091 A1 | 8/2007 | Boyer et al. | |
| 2007/0225807 A1 | 9/2007 | Phan et al. | |
| 2007/0233068 A1 | 10/2007 | Bruneau et al. | |
| 2007/0233081 A1 | 10/2007 | Pasquet et al. | |
| 2007/0233089 A1 | 10/2007 | DiPoto et al. | |
| 2007/0270834 A1 | 11/2007 | Bruneau et al. | |
| 2007/0276369 A1 | 11/2007 | Allard et al. | |
| 2007/0276493 A1 | 11/2007 | Malandain et al. | |
| 2007/0282443 A1 | 12/2007 | Globerman et al. | |
| 2008/0021457 A1 | 1/2008 | Anderson et al. | |
| 2008/0058934 A1 | 3/2008 | Malandain et al. | |
| 2008/0161818 A1 | 7/2008 | Kloss et al. | |
| 2008/0221685 A9 | 9/2008 | Altarac et al. | |
| 2008/0262617 A1 | 10/2008 | Froehlich et al. | |
| 2009/0234389 A1 | 9/2009 | Chuang et al. | |
| 2009/0270918 A1 | 10/2009 | Attia et al. | |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1138268 | 10/2001 |
| EP | 1138268 A1 | 10/2001 |
| EP | 1302169 A1 | 4/2003 |
| EP | 1330987 A1 * | 7/2003 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2 722 088 | 1/1996 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 | 4/2001 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 02/03882 A2 * | 1/2002 |
| WO | WO 03/057055 A1 | 7/2003 |
| WO | 2004/024010 | 3/2004 |
| WO | WO 2004/047689 A1 | 6/2004 |
| WO | WO 2004/047691 A1 | 6/2004 |
| WO | 2004/084768 A2 | 10/2004 |
| WO | WO 2005/009300 A1 | 2/2005 |
| WO | WO 2005/011507 A1 | 2/2005 |
| WO | WO 2005009300 A1 * | 2/2005 |
| WO | WO 2005/044118 A1 | 5/2005 |
| WO | WO 2005/048856 A1 | 6/2005 |
| WO | WO 2005/110258 A1 | 11/2005 |
| WO | 2006/064356 A1 | 6/2006 |
| WO | WO 2007/034516 A1 | 3/2007 |
| WO | 2007052975 A1 | 5/2007 |
| WO | 2009/083276 A1 | 7/2009 |
| WO | 2009/083583 A1 | 7/2009 |

WO 2009/098536 A1 8/2009

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," Spine, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spin Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," Spine, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerative del Rachide Lombare, Oct. 5-6, 2001 Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitemen des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Verté Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopépedique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spina Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," Spine, Jul. 1992, pp. 834-837, vol. 17, No. 7.

Kramer at al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," Spine, 1991, pp. S298-S301, vol. 16, No. 6, Supplement.

* cited by examiner

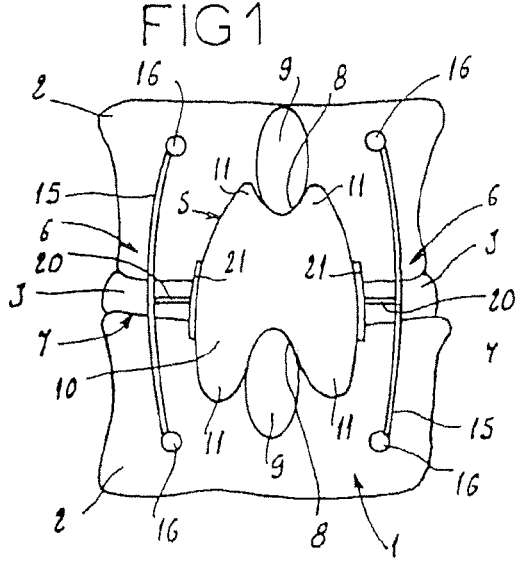
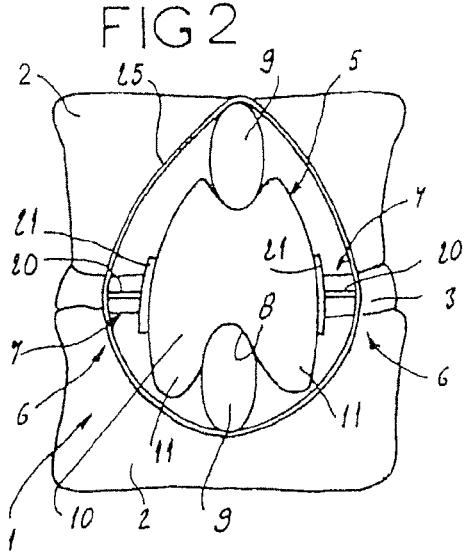
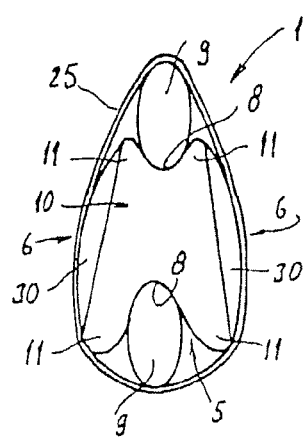
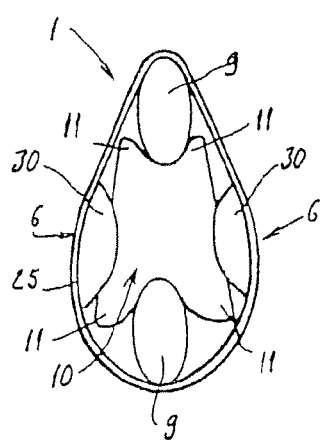

POSTERIOR VERTEBRAL SUPPORT ASSEMBLY

This application is a national phase filing of international application no. PCT/FR2003/002635, filed Sep. 3, 2003, which claims priority to French patent application no. 02 11189, filed Sep. 10, 2002.

The present invention concerns a posterior vertebral support assembly.

In the case of degeneration of the intervertebral disc of two vertebrae and/or of ligament distension, it is known to place a wedge between the spinous processes of the two vertebrae concerned, making it possible to support the vertebrae. In this regard, reference may be made to French Patent Applications Nos. FR 94 03716 and FR 98 02300 filed in the name of the proprietor of the present application.

The wedges according to these earlier patent applications are connected to the spinous processes of the two treated vertebrae by two independent ligaments, each of the ligaments passing through the wedge and tightly surrounding the corresponding spinous process. In the case of flexion of the spinal column in a forward direction, the spinous processes move away from one another, thereby causing longitudinal stretching of the wedge.

A drawback of this longitudinal stretching is that of stressing the wedge in longitudinal traction. The conditions of exertion of this traction can however be perfected, in particular in order to obtain assisted and contained control of the movement of the vertebrae, inasmuch as the repetition of this traction threatens to affect the durability of the wedge.

The present invention aims to remedy this drawback.

The assembly which it concerns comprises, in a manner known per se, an interspinous wedge configured to be inserted between the spinous processes of two vertebrae to be treated, whereof at least the zone designed to be placed between the spinous processes of the vertebrae is made of an elastically deformable material.

According to the invention, the assembly further comprises:
- two compressive lateral elements, designed to be placed on either side of the wedge in the longitudinal direction, the compressive lateral elements being deformable between releasing positions, which they occupy when the vertebrae are in lordosis or when the spinal column is extended, and wherein they are relatively spaced apart from the wedge in the transverse direction, and compressive positions, which they occupy when the spinal column is in flexion, and wherein they are relatively close to the wedge in the transverse direction; and
- two lateral transmission elements, placed between the compressive lateral elements and the wedge, configured in order, when the compressive lateral elements are displaced in said compressive position, to press against the wedge in the transverse direction thereof, at the zone of the wedge designed to be placed between the spinous processes of the vertebrae.

The assembly according to the invention thus makes it possible to exert a progressive transverse compression on the wedge during the movement of flexion of the spinal column. This compression will reduce the shear stresses which are exerted on the wedge during intervertebral distancing combining tilting and forward sliding movements, owing to the containment of the displacements effected by the wedge.

The transverse compression of the wedge is preferable to pure longitudinal traction from the point of view of durability of the wedge, since it compensates the stressing of the wedge in the longitudinal direction.

The zone of the wedge designed to be placed between the spinous processes may be made of a material having limit of compressibility in the transverse direction of the wedge, and the assembly may then be configured such that this limit is reached when the treated vertebrae attain a predetermined tilted position.

It is also possible to configure the compressive lateral elements so that the elements have a limit of deformation in the transverse direction, this limit of deformation being reached when the treated vertebrae attain a predetermined tilted position.

The compressive lateral elements may be deformed nonelastically or elastically between said releasing and compressive positions. In the latter case, the return force of the elements to their neutral form contributes to the damping of the tilting movement of the treated vertebrae.

The compressive lateral elements may likewise be elastically deformable in the longitudinal direction of the compressive lateral elements, to the same end.

According to one embodiment of the invention, the compressive lateral elements are independent of one another, and each is connected to one of the treated vertebrae by one end and to the other treated vertebra by its other end. The connection of the ends of the compressive lateral elements to the vertebrae may in particular be effected at the pedicles of the vertebrae, by means of pedicular screws engaged in eyelets or anchorage pieces included in the compressive lateral elements.

The connection of the compressive lateral elements to the vertebrae may also be effected, in the case of the overlying vertebra, by means of the passage of the elements beneath the laminae of that vertebra. This sub-laminal passage makes it possible to preserve the pedicles and to be as central as possible in order, during the longitudinal elongation, to optimize the transverse thrust exerted on the wedge. In the case of the underlying vertebra, these same compressive lateral elements may also be connected to an interpedicular transverse connecting bar, placed in position especially in the case of laminectomy on this vertebra, thus making it possible to reduce the concentration of strains. Similarly, the compressive lateral elements may be connected to a connecting bar joined to a system of arthrodesis of the two underlying vertebrae.

According to another embodiment of the invention, the compressive lateral elements are formed by the two lateral portions of a circular strap engaged round the spinous processes of the two treated vertebrae.

The lateral transmission elements themselves may be constituted by small bars bearing on the one hand against the compressive lateral elements and on the other hand against the wedge, especially via small support plates.

These same lateral transmission elements may likewise be constituted by bosses connected either to the compressive lateral elements or to the wedge. In the latter case, the bosses may be integral with the wedge.

The wedge may be made entirely of an elastically deformable material such as a silicone; it may in particular comprise a core made of such a material and a textile envelope containing the core.

The wedge may also be formed by a band of resilient material, suitably curved.

The wedge may comprise a spring placed transversely at its zone designed to be placed between the spinous processes.

For greater understanding thereof, the invention is described again hereinafter with reference to the appended diagrammatic drawing representing, by way of non-limiting example, several possible embodiments of the assembly concerned.

FIG. 1 is a rear view, very simplified, after the positioning on two vertebrae;

FIG. 2 is a view similar to FIG. 1, according to the second embodiment;

FIG. 3 is a view similar to FIG. 1, according to the third embodiment, only the spinous processes of the vertebrae being shown, and FIG. 4 is a view similar to FIG. 3, according to a variant.

FIG. 1 represents a posterior vertebral support assembly 1 placed in position on two vertebrae 2 affected by degeneration of the disc 3 and/or ligament distension.

The assembly 1 comprises an interspinous wedge 5, two compressive lateral elements 6 and two lateral transmission elements 7.

The wedge 5 is made of an elastically flexible material and comprises two curved recesses 8 allowing it to be inserted between the spinous processes 9 of the two vertebrae 2. It may in particular conform to the wedge according to French Patent Application No. FR 98 02300, that is to say:

- comprising a core made of silicone and an envelope made of polyester fabric,
- having an interspinous portion 10 having a height greater than the distance separating the spinous processes 9 when the vertebrae 2 are in lordosis in order to be compressed when the wedge 5 is inserted between the processes 9 and to permit relief of the disc 3 and also restoration of the ligaments to functional tension, and
- having lugs 11 which bound the curved recesses 8, the lugs 11 broadly enveloping the processes 9 and being self-tightened round the processes 9 when said interspinous portion 10 is compressed.

The wedge 5 shown in FIG. 1 differs, however, from the wedge according to the aforesaid French Patent Application No. FR 98 02300 in that it has domed lateral walls, imparting to it a relatively large width at said interspinous portion 10.

Each element 6 is formed by a lamina 15 made of elastically deformable synthetic material and by two eyelets 16 connected to the ends of the lamina 15. The latter is curved and comprises the element 7 at the median portion of its concave face, the concave face being designed to be turned towards the wedge 5.

The eyelets 16 are designed to receive pedicular screws permitting the anchorage of the elements 6 to the vertebrae 2.

Each element 7 is formed by a small rigid bar 20 fixed to an element 6, and is oriented substantially perpendicularly to the zone of the element 6 to which it is connected. The bar 20 is placed, after implantation, at the interspinous portion 10 of the wedge 5.

Each bar 20 is rigidly connected with a small plate 21 for bearing against the portion 10.

The assembly 1 according to the invention is in the position shown in FIG. 1 when the vertebrae 2 are in lordosis.

In the case of extension of the spinal column, the vertebrae 2 pivot in a direction in which the processes 9 are brought closer to one another, thereby leading to compression of the wedge 5 up to the limit of elasticity of the material constituting the core of the wedge. A damping of the pivoting movement of the vertebrae 2 is thus obtained as long as said limit of elasticity is not reached, then the arresting of that same movement is obtained when the limit of elasticity is reached. During this compression of the wedge 5, the elements 6 are deformed in the direction in which their curvature is increased, contributing to the damping of the movement of the vertebrae 2. The elements 6 likewise provide a perfect guarantee of maintenance of the position of the wedge 5 between the processes 9.

In the case of flexure of the spinal column, the vertebrae 2 pivot in a direction in which the processes 9 are spaced from each other, thereby leading to a reduction in the curvature of the elements 6. The elements 7 then press against the wedge 5 transversely, thereby also making it possible to dampen the movement of the vertebrae 2 then to arrest that movement when the limit of elasticity of the material forming the core of the wedge 5 is reached and/or when the elements come close to a substantially rectilinear form.

FIG. 2 shows an assembly 1 similar to that just described, except that the elements 6 are formed by the two lateral portions of a circular strap 25 engaged round the processes 9 of the vertebrae 2. The other portions or elements already described, which are to be found again in this second embodiment, are not described again and are designated by the same numerical references as before.

The strap 25 may be made of a slightly elastically stretchable material, and thus also contributes to the damping and then blocking of the pivoting movement of the vertebrae 2 in the case of flexion of the spinal column.

FIGS. 3 and 4 show a third embodiment of the assembly 1, in which the latter is similar to that shown in FIG. 2, except that the small bars 20 and plates 21 are replaced by bosses 30 along which pass the lateral portions of the strap 25. The bosses 30 may be fixed to the wedge 5 or be integral therewith, as shown in FIG. 3, or may be rigidly connected with the strap 25 and bear against the wedge 5, optionally at lateral recesses which the wedge includes to receive them, as shown in FIG. 4.

As it appears from the foregoing, the invention provides a decisive improvement on the prior art, by providing a posterior vertebral support assembly which does not stress the wedge in the longitudinal direction during the movement of flexion of the spinal column. Perfect control of the movement of the vertebrae is obtained by means of this assembly, and the durability of the wedge is not affected by the repeated movements of the vertebrae.

It is self-evident that the invention is not limited to the embodiment described above by way of example, but that on the contrary it encompasses all the variants of embodiment coming within the scope of protection defined by the appended claims.

The invention claimed is:

1. A posterior vertebral support assembly, comprising:
   an interspinous wedge configured to be inserted between the spinous processes of two vertebrae, wherein the wedge includes:
   first and second opposing ends, each end comprising a recess shaped to receive the respective spinous processes;
   a longitudinal axis extending through said recesses;
   first and second lateral sides extending from the first end to the second end; and
   at least one elastically deformable zone;
   two compressive lateral elements disposed on either lateral side of the wedge in a longitudinal direction, wherein the compressive lateral elements are deformable between releasing positions and compressive positions; and
   two lateral transmission elements disposed between the compressive lateral elements and the wedge, and configured to selectively press against the lateral sides of the wedge substantially midway between the first and second ends in a transverse direction near the elastically deformable zone; wherein a force applied by the lateral transmission elements against the wedge varies based on the relative spacing between the compressive lateral elements as they move between the releasing position and the compressive position in response to spinal flexion; each lateral transmission element disposed entirely on a respective lateral side of said longitudinal axis.

2. The support assembly of claim 1 wherein the zone has a limit of compressibility in the transverse direction, and wherein the limit is reached at a predetermined tilted position.

3. The support assembly of claim 1 wherein the compressive lateral elements have a limit of deformation in the transverse direction, and wherein the limit is reached at a predetermined tilted position.

4. The support assembly of claim 1 wherein the compressive lateral elements are elastically deformable between the releasing and compressive positions.

5. The support assembly of claim 1 wherein the compressive lateral elements are elastically deformable generally along an axis of the spine.

6. The support assembly of claim 1 wherein the compressive lateral elements are independent of one another, and wherein each element is connectable to a treated vertebra with one end and to another treated vertebra by its other end.

7. The support assembly of claim 1 wherein the compressive lateral elements include eyelets or anchorage pieces designed to receive pedicular anchorage screws.

8. The support assembly of claim 1 wherein the compressive lateral elements are adapted to pass beneath the laminae of the overlying vertebra.

9. The support assembly of claim 1 wherein the compressive lateral elements are deformable between releasing positions, which they occupy when the vertebrae are in lordosis or when the spinal column is extended, and wherein they are relatively spaced apart from the wedge in the transverse direction, and compressive positions, which they occupy when the spinal column is in flexion, and wherein they are relatively close to the wedge in the transverse direction.

10. The support assembly of claim 9 wherein the two lateral transmission elements are disposed in a manner to press against the wedge in the transverse direction when the compressive lateral elements are displaced in said compressive position.

11. The support assembly of claim 1 wherein displacement of the lateral transmission elements towards each other applies a compressive force to the wedge so as to urge the wedge first and second ends away from each other.

12. The support assembly of claim 1 wherein, when the spinous processes are received in the corresponding recesses, the lateral transmission elements do not cross a sagittal plane defined by the spinous processes in the space between the spinous processes.

13. The support assembly of claim 1 wherein the lateral transmission elements are bosses disposed between the compressive lateral elements and the wedge.

14. A posterior vertebral support assembly, comprising:
an interspinous wedge having:
a first end with a saddle-shaped receiver sized to receive and engage a spinous process of a first vertebra;
a second end longitudinally opposite the first end with a saddle-shaped receiver sized to receive and engage a spinous process of a second vertebra;
a longitudinal axis extending through said saddle-shaped receivers of said first and second ends;
an elastically deformable zone between the saddle-shaped receivers;
a first lateral side adjacent the deformable zone;
a second lateral side adjacent the deformable zone and opposite the first lateral side; the distance between the first and second ends being greater than the distance between the first and second lateral sides;
first and second longitudinally extending compressive lateral elements disposed adjacent to the lateral sides of the interspinous wedge, but entirely spaced away therefrom; the compressive lateral elements being deformable between releasing positions and compressive positions and each being sized to extend from the first vertebra to the second vertebra and being shaped to connect to both the first vertebra and the second vertebra;
two lateral transmission elements respectively disposed between the compressive lateral elements and the lateral sides of the deformable zone;
the two lateral transmission elements being configured to selectively increase and decrease loading against the lateral sides of the wedge near the elastically deformable zone in a direction transverse to the longitudinal axis when the compressive lateral elements move between the releasing and compressive positions.

15. The support assembly of claim 14 wherein the compressive lateral elements include eyelets or anchorage pieces designed to receive pedicle screws that connect the lateral transmission elements to the first and the second vertebrae.

* * * * *